(12) United States Patent
Mathur et al.

(10) Patent No.: US 7,158,235 B2
(45) Date of Patent: Jan. 2, 2007

(54) SYSTEM AND METHOD FOR INSPECTION USING WHITE LIGHT INTERFEROMETRY

(75) Inventors: Sanjeev Mathur, Irving, TX (US); Chu-Yin Chang, Plano, TX (US)

(73) Assignee: Rudolph Technologies, Inc., Flanders, NJ (US)

( * ) Notice: Subject to any disclaimer, the term of this patent is extended or adjusted under 35 U.S.C. 154(b) by 316 days.

(21) Appl. No.: 10/467,438

(22) PCT Filed: Dec. 5, 2001

(86) PCT No.: PCT/US01/43178

§ 371 (c)(1),
(2), (4) Date: Dec. 8, 2003

(87) PCT Pub. No.: WO03/058163

PCT Pub. Date: Jul. 17, 2003

(65) Prior Publication Data

US 2004/0090634 A1   May 13, 2004

(51) Int. Cl.
*G01B 9/02* (2006.01)

(52) U.S. Cl. ...... 356/497; 356/511

(58) Field of Classification Search ........ 356/497, 356/511–514, 489, 495, 450
See application file for complete search history.

(56) References Cited

U.S. PATENT DOCUMENTS

| 4,732,473 | A | | 3/1988 | Bille et al. | 356/237 |
|---|---|---|---|---|---|
| 4,818,110 | A | * | 4/1989 | Davidson | 356/512 |
| 5,402,234 | A | * | 3/1995 | Deck | 356/497 |
| 5,465,147 | A | | 11/1995 | Swanson | 356/345 |
| 5,808,735 | A | * | 9/1998 | Lee et al. | 356/237.2 |
| 5,953,124 | A | | 9/1999 | Deck | 356/357 |
| 6,020,965 | A | * | 2/2000 | Endo | 356/496 |
| 6,173,070 | B1 | | 1/2001 | Michael et al. | 382/145 |
| 6,195,168 | B1 | | 2/2001 | De Lega et al. | 356/497 |
| 6,275,297 | B1 | | 8/2001 | Zalicki | 356/496 |
| 6,580,514 | B1 | * | 6/2003 | Onuma et al. | 356/512 |
| 2001/0046054 | A1 | | 11/2001 | Zeylikovich et al. | 356/497 |
| 2002/0021438 | A1 | | 2/2002 | Isozaki et al. | 356/237.5 |
| 2002/0024661 | A1 | | 2/2002 | Zeimantz | 356/237.4 |
| 2002/0034325 | A1 | | 3/2002 | Reinhorn et al. | 382/145 |

FOREIGN PATENT DOCUMENTS

| DE | 41 08 944 A1 | 9/1992 |
|---|---|---|
| EP | 0 647 310 B1 | 10/1997 |
| JP | 08327327 A * | 12/1996 |
| WO | WO 99/01716 | 1/1999 |

(Continued)

OTHER PUBLICATIONS

Search Report for PCT/US01/43178 Dated Jul. 26, 2002 in parent PCT filing of U.S. application filed herewith.

*Primary Examiner*—Hwa (Andrew) Lee
*Assistant Examiner*—Marissa J. Detschel
(74) *Attorney, Agent, or Firm*—Dicke, Billig & Czaja, PLLC (57) ABSTRACT

A system for inspecting components is provided. The system includes an image data system that generates image data of the component, such as from a position overlooking the top of a bumped wafer. An interferometry inspection system is connected to the image data system and receives the image data, and analyzes the image data to locate interference fringing that is used to determine the surface coordinates of the bump contacts.

47 Claims, 5 Drawing Sheets

FOREIGN PATENT DOCUMENTS

| WO | WO 00/42381 | 7/2000 |
| WO | WO 01/42735 A1 | 6/2001 |

* cited by examiner

SYSTEM AND METHOD FOR INSPECTION USING WHITE LIGHT INTERFEROMETRY

FIELD OF THE INVENTION

The present invention pertains to the field of component inspection systems. More specifically, the invention relates to a system and method for component inspection that uses interferometry, such as white light interferometry, to measure three-dimensional features of the component.

BACKGROUND OF THE INVENTION

Inspection systems that use image data are known in the art. Such inspection systems typically use image data from a component that has been illuminated by either a coherent or noncoherent source, and then perform image analysis processes on the image data to determine whether the component conforms to predetermined criteria. For example, image data analysis is used to determine whether components have been properly marked, have features in the correct location, or have other specified criteria. In this regard, a "feature" can include a desired feature, such as a contact, or an undesired feature, such as damage on the contact that extends from or into the surface of the contact.

One problem with such component inspection systems is that three-dimensional aspects of the component must be inferred from the image data. Thus, in many cases it is difficult to determine whether an indication in the image data is from a feature that extends above or below a plane of reference. Likewise, since such image data analysis uses relative changes in brightness to infer the location of features and to determine whether such features fall within predetermined allowable criteria, it often occurs that the features are not distinguishable under a single lighting source. While it is known to use multiple lighting sources, such as lighting sources from two different angles, such lighting sources may still result in image data that does not clearly identify features of the component that do not meet specified criteria, such as to allow the size of features to be accurately determined.

SUMMARY OF THE INVENTION

In accordance with the present invention, a system and method for component inspection are presented that overcome known problems with component inspection.

In particular, a system and method for component inspection are provided that allow surface coordinates of the component to be determined using interferometery.

In accordance with an exemplary embodiment of the present invention, a system for inspecting components is provided. The system includes an image data system that generates image data of the component, such as from a position overlooking the top of a bumped wafer. An interferometry inspection system is connected to the image data system and receives the image data, and analyzes the image data to locate interference fringing that is used to determine the surface coordinates of the bump contacts.

The present invention provides many important technical advantages. One important technical advantage of the present invention is a system and method for inspecting components that uses interferometry to determine three-dimensional surface coordinates of the component. The present invention allows monochromatic or white light interferometry to be used to generate interference fringes on the component, where the third axis coordinates can be determined from interference fringing.

Those skilled in the art will further appreciate the advantages and superior features of the invention together with other important aspects thereof on reading the detailed description that follows in conjunction with the drawings.

DETAILED DESCRIPTION OF THE INVENTION

In the description that follows, like parts are marked throughout the specification and drawings with the same reference numerals, respectively. The drawing figures are not necessarily to scale, and certain components can be shown in generalized or schematic form and identified by commercial designations in the interest of clarity and conciseness.

Figure 1:
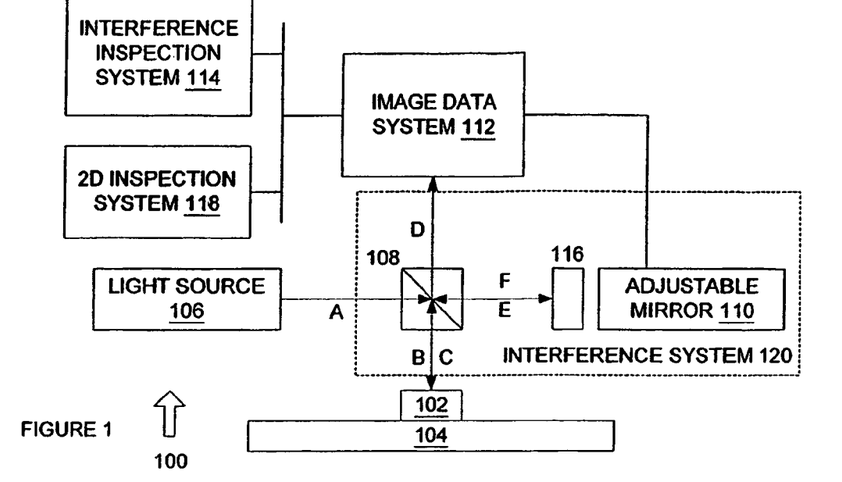
FIG. 1 is a diagram of a system for performing component inspection using interferometry in accordance with an exemplary embodiment of the present invention.

FIG. 1 is a diagram of a system 100 for performing component inspection using interferometry in accordance with an exemplary embodiment of the present invention. System 100 allows the three-dimensional surface coordinates of a component to be determined using interferometry, such as by using white light interference to create interference fringing on the component as a function of the height of features on the component.

System 100 includes component 102 on component support 104. Component support 104 can be a die support, a belt, a film frame, a tray, or any other suitable component inspection support. Component 102 can be a semiconductor component, a wafer, a die, a chip-scale package, a bumped wafer, a ball grid array, a packaged die, a die in gel pack, a die in a waffle pack or tray, or other suitable components in other suitable configurations. Component 102 is typically provided underneath interference system 120 by a suitable system or apparatus, such as a belt drive, robot arm, or other suitable systems or apparatuses.

System 100 includes light source 106, which can be a monochromatic light source, a polychromatic light source, a white light source, a coherent or noncoherent light source, or other suitable light sources. Light source 106 generates a beam of light travelling in direction "A." When retractable shutter 116 is in place in front of adjustable mirror 110, the beam of light "A" reflects off beam splitter 108 and travels in the direction of arrow "B." The light then illuminates component 102 and returns in the direction of arrow "C." The light then travels in direction "D" to image data system 112 where it is converted into an N×M array of pixels of brightness data, where "N" and "M" are integers, or other suitable image data. This image data is then provided to 2D inspection system 118 for 2D image analysis using the image data.

In addition, retractable shutter 116 can be removed from in front of adjustable mirror 110, such that the light also travels in direction "A" and then is split by beam splitter 108 so as to travel in direction "E" to adjustable mirror 110. The light is then reflected back along path "F" and reaches beam splitter 108, where the light is directed to component 102 along path "B," and the light from adjustable mirror 110 is then reflected back along path "C" and path "D" to image data system 112. Adjustable mirror 110 can include a motor with magnetic, optical, or other indicators that allow the displacement of the mirror to be correlated with the degree of rotation of the motor, can use precise location measurement (such as by laser) to determine the location of the mirror and corresponding surface coordinates, or other suitable procedures can be used to the location of the mirror.

As a result of the beam splitting and reflection, the image data generated by image data system 112 will include interference fringing. Interference fringing is a phenomenon caused when light from a component includes light that is out of phase with other light received from the component by a fractional wave length. For example, if the light is out of phase by 180° or one-half wavelength, then the brightness data will be significantly decreased, as the in-phase light will tend to cancel the out-of-phase light, such that the brightness decreases. For light that is out-of-phase by less than or greater than 180°, there will a decrease in brightness but the decrease will not be as significant. When the light is in-phase, the brightness will be increased. In one exemplary embodiment, adjustable mirror 110 can be formed from the material that is being inspected on component 102, such as a gold mirror for inspecting contact bumps made of gold, to improve the quality of interference fringing patterns generated using white light interferometry. The improved quality is obtained by using the same material for the mirror as is being inspected because this configuration reduces the absorption of light wavelengths that create the interference that occurs when dissimilar materials are used.

Using this interference principle, adjustable mirror 110, component support 104, or other suitable components of system 100 can be moved so as to create a changing interference pattern on component 102. For example, if adjustable mirror 110 is moved towards beam splitter 108, then the phase difference in the in-phase and out-of-phase light received at image data system 112 will change as adjustable mirror 110 moves. Thus, interference fringing will occur on the illuminated portions of the surface of component 102. The interference fringes will appear as increasing and decreasing brightness at various points of the surface of component 102. Thus, the brightness values of the N×M pixels of image data generated by image data system 112 will vary as adjustable mirror 110 is moved towards beam splitter 108. In this manner, it is possible to generate successive frames of image data using image data system 112 as adjustable mirror 110 is moved towards beam splitter 108 so as to determine the change in brightness of each pixel of the image data as a function of the location of adjustable mirror 110. The coordinates of the surface of component 102 at a location corresponding to each pixel can thus be determined by locating the center of the interference fringing based on the brightness of each pixel in successive images generated by image data system 112 and correlating that to the location of adjustable mirror 110. Known surface coordinate values can be used to calibrate adjustable mirror 110.

Image data system 112 is coupled to interferometry inspection system 114, 2D inspection system 118, and interference system 120. As used herein, the term "couple," and its cognate terms such as "couples" and "coupled," can include a physical connection (such as through one or more copper conductors), a virtual connection (such as one or more randomly assigned data memory locations of a data memory device), a logical connection (such as through one or more logical devices of a semiconducting circuit), a wireless connection, a hypertext transfer protocol (HTTP) connection, other suitable connections, or a suitable combination of such connections. In one exemplary embodiment, systems and components can be coupled to other systems and components through intervening systems and components, such as through an operating system of a general purpose processing platform.

Interferometry inspection system 114 can be implemented in hardware, software, or a suitable combination of hardware and software, and can be one or more software systems operating on a video data processing platform, such as the Matrox Genesis LC available from Matrox of Dorval, Quebec. Interferometry inspection system 114 receives the successive sets of image data from image data system 112 and performs an analysis on the brightness data of each pixel to determine the surface coordinate data for the surface points of component 102 corresponding to each pixel. Likewise, adjustable mirror 110 generates adjustable mirror location data that is provided to interferometry inspection system 114 through image data system 112 or other suitable systems or components, so as to allow interferometry inspection system 114 to generate three-dimensional coordinates for the surface of each pixel of the N×M data image data. In this manner, a three-dimensional map of the surface coordinates of component 102 can be generated using interference principles.

In operation, a component 102 is inspected using two-dimensional and three-dimensional techniques. In one exemplary embodiment, the component can first be inspected using two-dimensional techniques, and if the results of the two-dimensional techniques are indeterminate, then three-dimensional mapping of the component can be performed. Thus, image data system 112 can cause retractable shutter 116 to be removed so as to switch to from a 2D inspection mode to a 3D inspection mode. Image data system 112 further provides control data to adjustable mirror 110 to cause adjustable mirror 110 to begin tracking at a predetermined rate, in predetermined steps, or in other suitable manners. Image data system 112 then generates a successive sequence of N×M pixel sets of image data of component 102 as adjustable mirror 110 tracks at the predetermined rate or in other manners. These sets of image data are provided to interferometry inspection system 114, which can determine the surface coordinates corresponding to each pixel using interference principles and the known location of adjustable mirror 110.

After all sets of image data have been generated by adjustable mirror 110, image data system 112 generates suitable control commands, or a local controller of adjustable mirror 110 causes adjustable mirror 110 to return to a predetermined location and to replace retractable shutter 116. Likewise, adjustable mirror 110 can be operated in two modes, such as one where image data is generated as adjustable mirror 110 moves towards beam splitter 108, and a second mode in which image data is generated as adjustable mirror 110 is moved away from beam splitter 108. In this manner, resetting adjustable mirror 110 is unnecessary.

Figure 2:
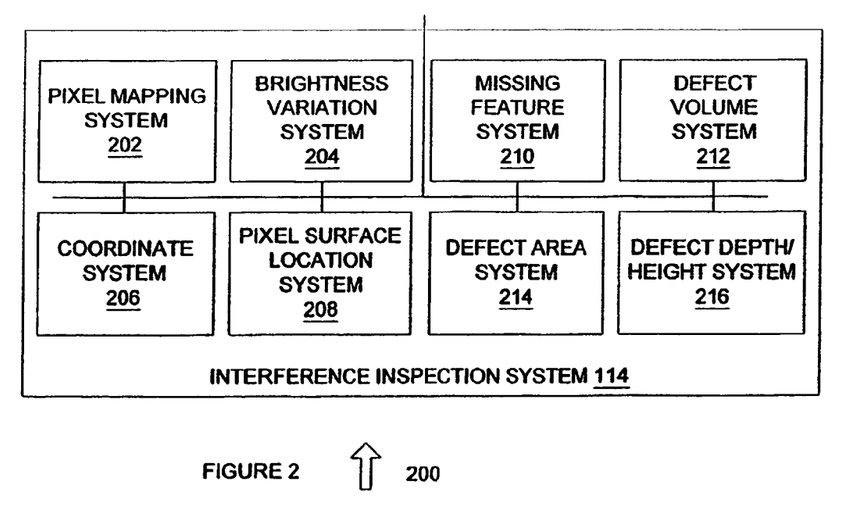
FIG. 2 is a diagram of a system for analyzing image data using interferometry in accordance with an exemplary embodiment of the present invention.

FIG. 2 is a diagram of a system 200 for analyzing image data using interferometry in accordance with an exemplary embodiment of the present invention. System 200 allows two or more sets of image data to be analyzed to determine the surface coordinates of one or more pixels, such as pixels in an N×M pixel array or other suitable pixels or sets of pixels.

System 200 includes interferometry inspection system 114 and pixel mapping system 202, brightness variation system 204, coordinate system 206, pixel surface location system 208, missing feature system 210, defect volume system 212, defect area system 214, and defect depth/height system 216, each of which can be implemented in hardware, software, or a suitable combination of hardware and software, and which can be one or more software systems operating on a general purpose processing platform. As used herein, a software system can include one or more objects, agents, threads, subroutines, separate software applications, machine readable code, source code, executable code, two or more lines of code or other suitable software structures operating in two or more separate software applications, on two or more different processors, or other suitable software architectures. In one exemplary embodiment, a software system can include one or more lines of code or other suitable software structures operating in a general purpose software application, such as an operating system, and one or more lines of code or other suitable software structures operating in a specific purpose software application. In another exemplary embodiment, a software system can be one or more lines of hypertext markup language (HTML), extensible markup language (XML), a web browser plug-in, or other suitable code that operates in conjunction with a web browser application.

Pixel mapping system 202 receives surface coordinate data for each pixel in an N×M pixel array and generates a three-dimensional image of the component corresponding to the N×M pixel array. In one exemplary embodiment, pixel mapping system 202 can generate a user readable display to allow an operator to determine whether an item has acceptable or unacceptable characteristics, such as to determine the size of a scratch on a bump contact surface, other types of damage to bump contacts, or other types of damage to a component. Pixel mapping system 202 can also perform a preliminary analysis of the surface data of the component, such as to determine the area of suspected damage, the depth of suspected damage, or other user-selected characteristics, and can request operator assistance when such user-selected characteristics have "borderline" values or exceed acceptable values. Pixel mapping system 202 can further determine the volume of a damaged area, such as by determining the discrete incremental volume for each pixel surface based on the difference between where the surface is expected and where the surface is located. In this manner, pixel mapping system 202 can allow a user to specify an acceptable damage volume, and can accept or reject components based upon the volume of damage to the component or features of the component.

For example, where the component is a semiconductor die and the feature is a bump contact constructed from gold, the expected height of the bump contact can be, for example, 20 micrometers. Likewise, each pixel can cover a predetermined surface area, such as 25 square microns. Thus, a user can select a pass/fail criterion based on the volume of a scratch or indent to the surface of the gold bump, a burr or nodule on the surface of the gold bump, or other selected types of damage, based upon the volume of the damaged area. In this exemplary embodiment, if a scratch results in surfaces below 20 micrometers, then the height of contiguous pixels can be used and multiplied times an area of 25 square microns, where the volume is equal to the difference between 20 micrometers and the actual height of the surface corresponding to the pixel. The sum of each such area per contiguous pixel can then be added, such that the approximate volume of the material missing can be determined. A similar process can be used to determine the volume of nodules, burrs or other features extending above the surface. In this manner, feature acceptance criterion can be based upon damage volume data.

Brightness variation system 204 determines brightness variations between pixels in successive image data sets. In one exemplary embodiment, brightness variation system 204 can be used to generate a two-dimensional plot of brightness variation as a function of height for a single pixel. For example, brightness variation system 204 can retrieve brightness data for a pixel from each image data set, and the brightness data for a pixel can be plotted as a function of the location of adjustable mirror 110. The surface coordinates of the surface of the component corresponding to the pixel can then be determined from the variations in brightness caused by interference fringing and the coordinates of adjustable mirror 110, component support 104, or other suitable systems or components. In this manner, brightness variation system 204 can form sets of brightness data for each pixel that can be analyzed to determine the surface coordinates of the component corresponding to the location of that pixel. Brightness variation system 204 can also generate a plot showing the brightness variation for each pixel. Brightness variation system 204 can also compress pixel brightness data, such as by receiving successive frames of image data and compressing the image data for each pixel where variations between successive frames are within a predetermined tolerance. In this manner, brightness variation system 204 can reduce the data storage requirements for a set of image data, increase the speed of processing the image data, and provide other benefits. In one exemplary embodiment, brightness variation system 204 can receive 1,000 sets of image data, where each set includes an N×M array of pixel brightness data values. In this exemplary embodiment, the number of sets of image data required to determine the surface coordinates for the surface of the component corresponding to any given pixel may be a fraction of the number of sets, such as 50. Brightness variation system 204 can determine the sets of image data for each pixel having the data required to locate the surface for that pixel, and can discard data for that pixel in other sets, such as by using three-dimensional array data compression techniques or other suitable data compression techniques.

Coordinate system 206 determines the Z-axis coordinates for sets of pixel data, and can generate control data for controlling the position of the adjustable mirror 110, the component support 104, or other system or component that is used to generate interference fringing so as to determine the surface coordinates. In one exemplary embodiment, coordinate system 206 can determine the height or Z-axis coordinate of each N×M array or frame of pixel data, regardless of the manner in which the frames of pixel data are generated (where the N and M array positions are used to determine the X- and Y-axis coordinates, respectively). Thus, an adjustable mirror, an adjustable component support 104, or other suitable adjustable features can be used to control the relative location of each frame of pixel data along the Z-axis. Coordinate system 206 can also generate control data for controlling the location of the adjustable component, such as the surface of an adjustable mirror 110. In this exemplary embodiment, coordinate system 206 can cause the adjustable mirror 110 or other suitable systems or components to move through areas in which image data is not expected, such as to "fast forward" the sets of image data through areas in which no pixel surface changes are expected, such as along the length of a gold bump in the axial direction extending above the surface, up to within an expected area in which component feature surfaces are expected.

Pixel surface location system 208 receives brightness data from brightness variation system 204 or other suitable systems and determines the set of pixel data that identifies the surface coordinates of a point on a component that is associated with a given pixel using interferometry principles. In one exemplary embodiment, pixel surface location system 208 analyzes the N×M set of pixel data from frame to frame, and determines the pixels in each frame that identify coordinates of points on the surface of the component. In another exemplary embodiment, pixel surface location system 208 analyzes sets of pixel data, and determines the pixels in each set of pixel data that identify points on the surface of the component based on one or more sets of pixel data that precede or follow the set of data in which the surfaces are located. In this exemplary embodiment, pixel surface location system 208 can determine variations in pixel brightness, and can determine the surface corresponding to each pixel based upon the maximum variation, an interpolated point at which the maximum variation would occur, the indication of a center fringe of an interference pattern based upon changes in pixel brightness data, or other suitable data. Likewise, pixel surface location system 208 can analyze sets of pixel data over successive frames on a pixel by pixel basis, such as where all sets of data are first stored and then analyzed.

Missing feature system 210 receives surface coordinate data and generates missing feature data. In one exemplary embodiment, missing feature system 210 receives surface coordinate data for each of the pixels and determines whether a feature is missing based on the surface coordinate data, such as by determining whether a predetermined number of pixels do not have associated surface coordinates, by determining that the surface coordinate data is not consistent with the expected surface coordinate data for the feature, or by other suitable procedures. Missing feature system 210 can generate inspection pass/fail data indicating whether the inspection results are acceptable, borderline, or unacceptable, can generate notification data to notify an operator of the missing feature, or can generate other suitable data.

Defect volume system 212 receives surface coordinate data and generates defect volume data. In one exemplary embodiment, defect volume system 212 receives surface coordinate data for each of the pixels and determines the volume of a scratch or other defect into the surface, a nodule or other defect out of the surface, a mouse bite or other defect on the side of a feature, or other types of defects based on the surface coordinate data, such as by determining the difference between the expected and actual surface coordinate data for each pixel and by summing the associated volumes for pixels with such discrepancies, or by other suitable procedures. Defect volume system 212 can generate inspection pass/fail data indicating whether the inspection results are acceptable, borderline, or unacceptable, can generate notification data to notify an operator of the missing feature, or can generate other suitable data.

Defect area system 214 receives surface coordinate data and generates defect area data. In one exemplary embodiment, defect area system 214 receives surface coordinate data for each of the pixels and determines the area of a scratch or other defect into the surface, a nodule or other defect out of the surface, a mouse bite or other defect on the side of a feature, or other types of defects based on the surface coordinate data, such as by determining the surface area for contiguous groups of pixels having actual surface coordinate data above or below expected surface coordinate values or by other suitable procedures. Defect area system 214 can generate inspection pass/fail data indicating whether the inspection results are acceptable, borderline, or unacceptable, can generate notification data to notify an operator of the missing feature, or can generate other suitable data.

Defect depth/height system 216 receives surface coordinate data and generates defect depth or height data, as appropriate. In one exemplary embodiment, defect depth/height system 216 receives surface coordinate data for each of the pixels and determines the depth of a scratch or other defect into the surface, the height of a nodule or other defect out of the surface, the extent of a mouse bite or other defect on the side of a feature, or other types of defects based on the surface coordinate data, such as by determining the difference between the expected and actual surface coordinate data for each pixel and determining the maximum depth/height, the average depth/height, or by other suitable procedures. Defect depth/height system 216 can generate inspection pass/fail data indicating whether the inspection results are acceptable, borderline, or unacceptable, can generate notification data to notify an operator of the missing feature, or can generate other suitable data.

In operation, system 200 allows image data to be analyzed to determine surface coordinates of a component corresponding to one or more pixels in an N×M set of pixel data. System 200 uses two or more frames of N×M sets of pixel data to locate a surface of the component corresponding to each pixel. In this manner, system 200 allows three-dimensional mapping of component surfaces to be performed that enables accurate estimations of the volume of areas extending below or above the surface of a feature and otherwise allows for an accurate estimation of the three-dimensional features of a component.

Figure 3:
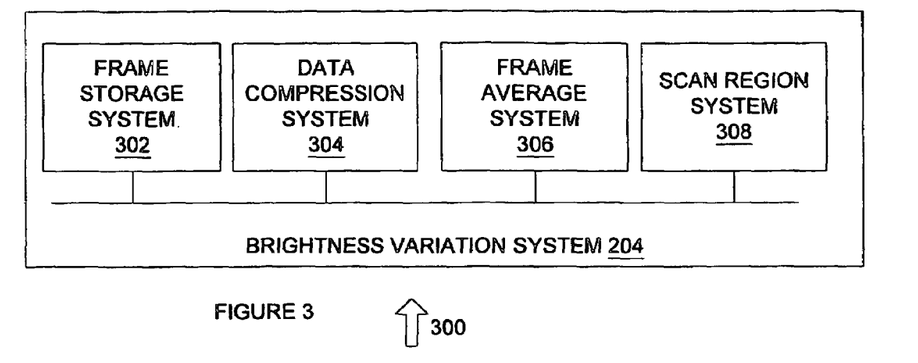
FIG. 3 is a diagram of a system for determining brightness variations in accordance with an exemplary embodiment of the present invention.

FIG. 3 is a diagram of a system 300 for determining brightness variations in accordance with an exemplary embodiment of the present invention. System 300 includes brightness variation system 204 and frame storage system 302, data compression system 304, frame average system 306, and scan region system 308, each of which can be implemented in hardware, software, or a suitable combination of hardware and software, and which can be one or more software systems operating on a general purpose processor platform.

Frame storage system 302 receives 2 or more frames of pixel data; where each frame can include an N×M array of pixel data. In one exemplary embodiment, the coordinates of a pixel in each successive frame of pixel data correspond to an area having known (x,y,z) coordinates on the surface of the component or other item that is being inspected. In this manner, variations between pixel brightness in successive frames can be analyzed to determine the surface coordinates of a point on the surface of the component. Likewise, frame storage system 302 can store a three-dimensional array of pixel brightness values, such that individual sets of pixel data at predetermined coordinate locations can be retrieved and analyzed. For example, each frame of pixel data can include (x,y) coordinate pixel data. Likewise, the z-axis location of each frame can be known or inferred from data such as an adjustable mirror 110 movement rate, a position controller system, or other suitable systems. In this manner, frame storage system 302 can store a three-dimensional array of brightness data where each point in the array corresponds to a predetermined location in the (x,y,z) coordinate system. Frame storage system 302 allows analysis of variations between individual pixels along the z-axis, rows of pixels along the x- or y-axis, sets of pixel data, such as a set of pixel data extending in a predetermined direction along the x- and y-axis in successive data frames along the z-axis, or other combinations of data.

Data compression system 304 can be used to compress data stored in frame storage system 302 or other suitable systems. In one exemplary embodiment, data compression system 304 can determine whether variations in pixels having identical (x,y) coordinates in successive z-axis data frame locations are within predetermined allowable variations, such that pixels indicative of no brightness variation can be eliminated so as to reduce data storage requirements. In one exemplary embodiment, data compression system 304 can look at successive frames of data to make this determination, Such as where pixel brightness variations over a series of two or more pixels must be analyzed to determine whether the pixels of data are significant for determining the surface coordinates of the component being inspected. Data compression system 304 can also compress data for storage after a component has been inspected, such as by using surface location data that has been confirmed to eliminate unnecessary data from a data set.

Frame average system 306 generates moving average data from the pixel brightness data that is used to determine the surface coordinate data corresponding to each pixel. In one exemplary embodiment, frame average system 306 subtracts an average offset value, such as by using the brightness data for pixels from the first several frames of data as the average or by other suitable procedures. Frame average system 306 then takes the absolute value of brightness data after such average value is subtracted, stores a moving average of the brightness data for the last five frames of data generated for each pixel, and detects when the moving average decreases by a predetermined amount. The surface corresponding to that pixel can then be determined to correlate to the location of the third previous frame. Likewise, other suitable numbers of frames can be used, other suitable mathematical operations can be performed on the successive pixel brightness data values, or other suitable processes can be performed to allow surface coordinate data for each pixel to be determined on the fly.

Scan region system 308 generates scan region data based on wafer tilt data, adaptive scan data, and other suitable data. In one exemplary embodiment, wafer tilt data is generated based on surface coordinate measurements at predetermined locations of a wafer, such as to determine wafer tilt caused by the wafer support, wafer surface variations, or other sources of tilting. It can be determined from this data that one side of the wafer is higher than the opposite side of the wafer, such as by 25 micrometers. Scan region system 308 adjusts the scan region, such as for scanning to locate the surface of a bump contact where the expected height of the bump surface is known, so as to optimize the number of frames of data that are generated and analyzed. In this exemplary embodiment, the scan region may encompass 30 frames of data that are taken in the region where the surface of bump contacts is expected. Because of the wafer tilt, the 30 frame region encompassing the surface coordinates of bump contacts on one side of the wafer may lie at a location that is above or below the 30 frame region encompassing the surface coordinates of bump contacts on the other side of the wafer, because of wafer tilt or other factors. Scan region system 308 adjusts the scan region to compensate for such wafer tilt or other factors.

Scan region system 308 can also generate adaptive scan data, such as by determining whether the surface coordinates of the feature are being located near the middle of the scan region. In one exemplary embodiment, the scan region can include generation of frames of brightness data at 30 locations, where the surface coordinates for each pixel are expected to be in the vicinity of the fifteenth frame. Scan region system 308 can determine whether the surface coordinates are being detected away from this expected location, such as at the fifth frame or at the twenty-fifth frame, and can adjust the scan region to adapt for wafer warpage, tilt, or other variations.

In operation, system 300 allows brightness variations in pixels to be analyzed and stored as sets of pixel data. System 300 further supports data compression techniques, such as data compression techniques that look at changes in brightness between a present and previous pixel value in two (x,y) arrays, data compression techniques that look at two or more sets of data and determine from brightness variation parameters whether the data can be compressed, techniques using a moving average to determine surface coordinate data corresponding to each pixel, or other suitable surface coordinate location techniques. System 300 further provides the stored data to other systems for analysis, such as to a mirror position system, pixel surface location system, pixel mapping system, or other suitable systems.

Figure 4:
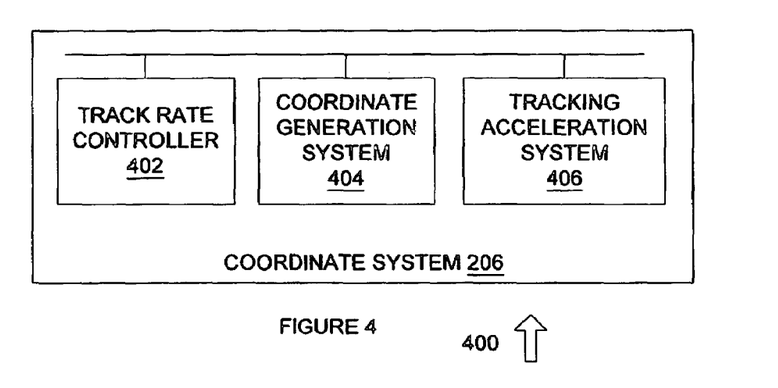
FIG. 4 is a diagram of a system for determining and controlling the position of a mirror or other systems or components that are used to create interference fringing, in accordance with an exemplary embodiment of the invention.

FIG. 4 is a diagram of a system 400 for determining and controlling the position of a mirror or other systems or components that are used to create interference fringing, in accordance with an exemplary embodiment of the present invention. System 400 includes coordinate system 206 and track rate controller 402, coordinate generation system 404, and tracking acceleration system 406, each of which can be implemented in hardware, software, or a suitable combination of hardware and software, and which can be one or more software systems operating on a general purpose processing platform.

Track rate controller 402 controls the track rate of systems or components that define the coordinates of a set of pixel data. In one exemplary embodiment, track rate controller 402 can be used to control the track rate of an adjustable mirror 110, so as to control the number of frames of data that are generated over the scan length of the component. In one exemplary embodiment, the number of frames of data that are generated can determine the resolution of the system, such that in systems in which less resolution is required, the track rate can be increased to decrease the number of frames of data. Likewise, track rate controller 402 can be used to monitor the track rate to confirm that the track rate is staying constant, or to generate compensation data for any changes in track rate and to provide the compensation data to coordinate generation system 404 or other suitable systems.

Coordinate generation system 404 generates z-axis coordinate data for successive frames of pixel data. In one exemplary embodiment, coordinate generation system 404 receives track rate data from track rate controller 402 and determines the expected and actual coordinate separation between successive frames of data along the z-axis. In this exemplary embodiment, coordinate generation system 404 can compensate for any variations in track rate, so as to correct the actual coordinate locations based on measured differences. Likewise, coordinate generation system 404 can determine the coordinates for successive frames along the z-axis from the movement of other suitable components or systems, such as a component support 104.

Tracking acceleration system 406 allows the time required for inspection of components to be optimized by accelerating tracking through areas in which damage to the component is not expected or would otherwise be detected by subsequent scanning. In one exemplary embodiment, a component can include features such as gold bumps or other features that are to be inspected for various defects. For example, one defect that may occur with a gold bump is a "mouse bite," where a section of the gold bump is missing. In this exemplary embodiment, the surface in the section of the gold bump that has the "mouse bite" would be at or near the base of the component die, such that it is only necessary to scan the surface of the component die extending up for a short length in order to detect this condition. If there are no other damage mechanisms that can result in damage at z-axis coordinates between the base and the top of the gold bump, then it is only necessary to scan the top of the gold bump after the base has been scanned. In this exemplary embodiment, the generation of image data along the z-axis is not required other than in the area of the top of the gold bump. Tracking acceleration system 406 can accelerate the position of an adjustable mirror 110 or other suitable components or systems so as to "fast forward" through areas where inspection is not required, and can further provide data to image data system 112 so that image data sets are not generated for these locations. In this manner, the generation and inspection of components can be optimized, so as to focus the generation of image data only on those areas that are necessary to determine whether the component has passed or failed inspection.

In operation, system 400 controls the position of a mirror or other suitable components so as to allow (x,y,z) coordinates to be accurately tracked and monitored. System 400 further allows tracking to be accelerated through areas in which inspection is unnecessary, so as to reduce the amount of data that needs to be generated and analyzed.

Figure 5:
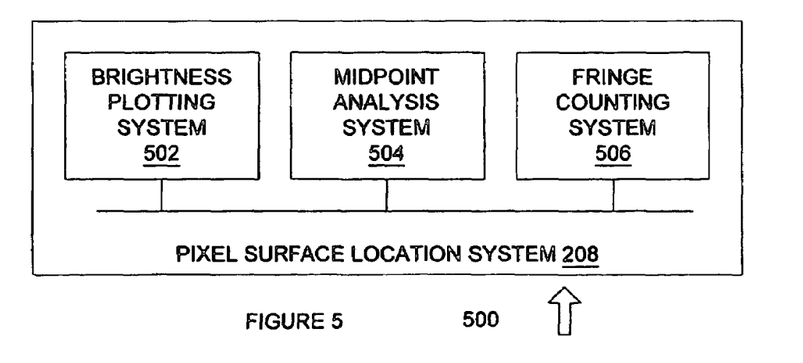
FIG. 5 is a diagram of a system for determining surface coordinates of a component corresponding to pixels of image data in accordance with an exemplary embodiment of the present invention.

FIG. 5 is a diagram of a system 500 for determining surface coordinates of a component corresponding to pixels of image data in accordance with an exemplary embodiment of the present invention. System 500 includes pixel surface location system 208 and brightness plotting system 502, midpoint analysis system 504, and fringe counting system 506, each of which can be implemented in hardware, software, or a suitable combination of hardware and software, which can be one or more software systems operating on a general purpose processing platform.

Brightness plotting system 502 plots the variations in brightness for successive sets of pixel data. In one exemplary embodiment, brightness plotting system 502 receives brightness values for successive z-axis locations of a pixel at (x,y) coordinates, so as to analyze a single set of z-axis variations for that pixel. In this manner, brightness plotting system 502 performs a pixel by pixel analysis to determine the corresponding surface location for each pixel. Brightness plotting system 502 can further generate user readable displays, such as to allow a user to see the variation in brightness values for a given pixel along the z-axis.

Midpoint analysis system 504 determines the midpoint of an interference pattern generated for each pixel. In one exemplary embodiment, midpoint analysis system 504 can receive a set of pixel brightness data variations along the z-axis for a single pixel, and can analyze the set of pixel brightness data variations to determine the midpoint, such as where the midpoint is the mathematical midpoint or halfway point between the two ends. Likewise, the midpoint can be determined by counting or determining the number of maxima and minima in brightness values that occur between the two end points, and by assigning the midpoint to the actual or theoretical location where the midpoint would occur based on the other data, such as by using envelope fitting, curve fitting, or other suitable techniques. Midpoint analysis system 504 can also process sets of pixel data, such as a subset of the (N×M) set of pixel data of each frame, the entire frame, or other suitable combinations.

Fringe counting system 506 performs a fringe counting analysis on sets of pixel data to determine the surface of the component corresponding to each pixel. In one exemplary embodiment, fringe counting system 506 can store suitable data, such as a magnitude and direction of brightness values above or below the average brightness value. In this exemplary embodiment, fringe counting system 506 can store a single set of brightness values, and can modify the brightness values based on each successive frame of brightness values along the z-axis. Fringe counting system 506 can be used where storage of the (x,y,z) array of data is not required, such as where surface data corresponding to each pixel can be determined based on analysis of successive frames of pixel data as they are measured.

In operation, system 500 performs analysis of pixel data to determine the surface of a component corresponding to each pixel in an N×M pixel array. System 500 allows the user to view data displaying variations along a z-axis for a given pixel or for sets of pixels, and can perform midpoint analysis, fringe counting, or other suitable functions so as to locate the surface of the component that corresponds to each pixel in the pixel array.

Figure 6:
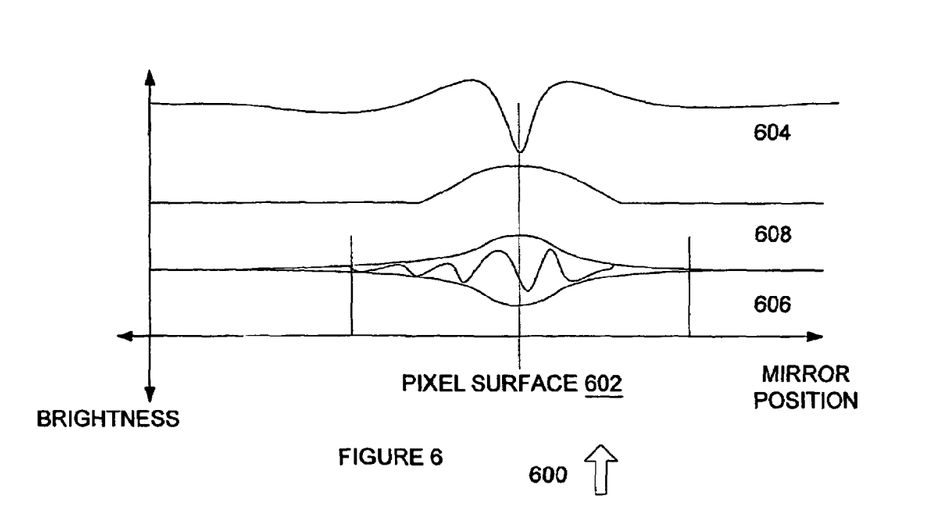
FIG. 6 is a pixel brightness variation diagram in accordance with teachings of an exemplary embodiment of the present invention.

FIG. 6 is a pixel brightness variation diagram 600 in accordance with teachings of an exemplary embodiment of the present invention. Pixel brightness variation diagram 600 includes a mirror position axis and a brightness axis. As shown, the variation in pixel brightness 604 is flat as mirror position increases until interference fringing begins to occur. The interference fringing causes the pixel brightness values to increase to a maximum, decrease to a minimum corresponding to pixel surface 602, and then increase to a maximum again prior to returning to a mid line value. In this exemplary embodiment, these three interference fringes allow the surface of the component corresponding to the pixel to be determined. One of ordinary skill in the art will realize that pixel brightness variation 602 is exemplary only, and that the actual pixel brightness variation measurements will not necessarily fall on a smooth curve as shown and will not necessarily have only 3 interference fringes, but may instead include a large number of variations. Thus, an envelope analysis such as shown in envelope 606 could be used to estimate pixel surface 602. Likewise, the end points of the envelope can also be used, such as by determining that the pixel surface 602 corresponds to the midpoint of the envelope. In another exemplary embodiment, a moving average brightness 608 can be used, where the coordinates of pixel surface 602 are determined from the location at which the moving average decreases by a predetermined amount. Likewise, other suitable analysis procedures can be used to determine the surface coordinates corresponding to a pixel location.

Figure 7:
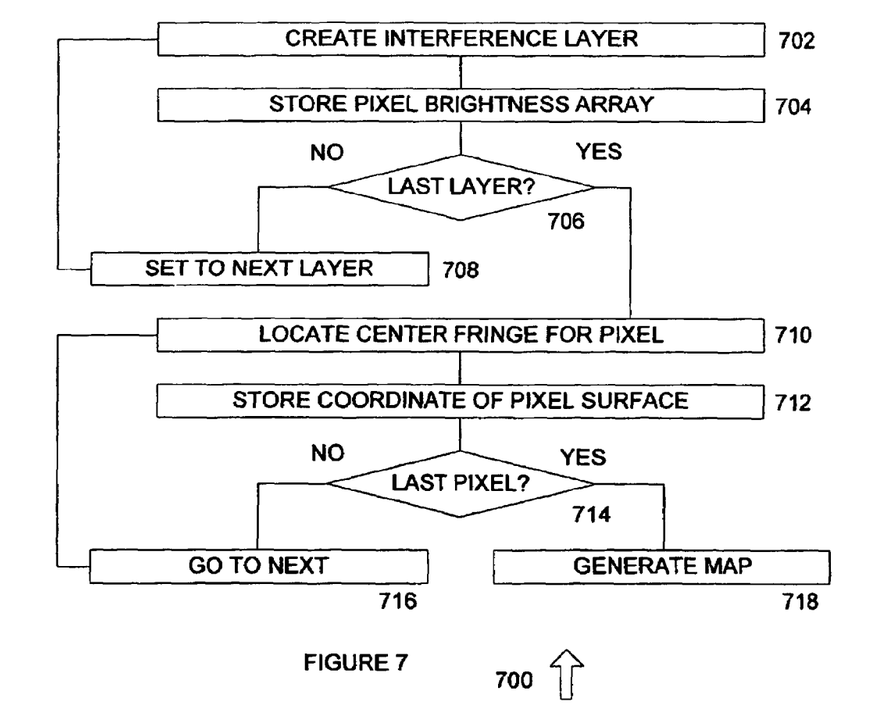
FIG. 7 is a flowchart of a method for determining surface coordinates of a component using interferometry in accordance with an exemplary embodiment of the present invention.

FIG. 7 is a flowchart of a method 700 for determining surface coordinates of a component using interferometry in accordance with an exemplary embodiment of the present invention. Method 700 begins at 702 where an interference layer is generated. In one exemplary embodiment, the interference layer can be created using a beam splitter and adjustable mirror, with white light so as to reduce the number of fringes and simplify the process of locating the center point of the interference pattern, or other suitable interference procedures can be used. The method then proceeds to 704.

At 704, a pixel brightness array is stored. In one exemplary embodiment, the pixel brightness array can include an N×M array of pixel brightness values, such as where the number of pixels per unit area provides sufficient resolution to perform inspection of the component. The method then proceeds to 706.

At 706, it is determined whether an N×M array of pixel data for the last z-axis location has been generated. In one exemplary embodiment, a predetermined number of N×M arrays of pixel data can be generated at locations along a z-axis, such as every 0.5 micrometers when a resolution of 0.5 micrometers is required, or at other suitable intervals. In this exemplary embodiment, a component having features that extend X micrometers above the surface would require on the order of X/2 +/− a tolerance factor of successive frames of data to be generated so as to generate surface data for mapping the component's surface. If the last layer has been generated, the method proceeds to 710. Otherwise, the method proceeds to 708, where the system is set to the next layer. In one exemplary embodiment, layers of imaged data can be generated by moving a mirror at a set rate, such that the mirror rate is not changed, but data settings for storage of the next N×M pixel array are changed. Likewise, variations in mirror motion rate can be tracked so as to generate correction data for locations, a stepper motor can be used and can be caused to step to the next position, or other suitable procedures can be used. The method then returns to 702.

At 710, the center fringe of the interference array is generated or determined for each pixel. In one exemplary embodiment, the set of pixel data along the z-axis for each pixel can be analyzed to locate the center fringe, such as by forming an envelope and determining the midpoint of the envelope, locating variations in pixel brightness data that exceed predetermined tolerances and then determining the center point based on the end points of the variations, by determining the magnitude and direction of the variation from a midpoint and determining whether the brightness value variations are increasing or decreasing in magnitude, or by other suitable processes. The method then proceeds to 712.

At 712, the coordinates of the surface of the component corresponding to the pixel are stored. In this exemplary embodiment, the coordinates can be stored in an N×M array, such that the array is filled in as the component is analyzed and analysis is terminated when the data in the array is sufficient to determine whether the component is acceptable or not acceptable. The method then proceeds to 714.

At 714, it is determined whether the last pixel has been analyzed. In one exemplary embodiment, pixels can be analyzed as they are measured, in groups, individually, or in other suitable manners. If it is determined at 714 that the last pixel has not been analyzed, the method proceeds to 716, where the next pixel or group of pixels is selected. The method then returns to 710. Otherwise, if it is determined at 714 that the last pixel has been analyzed, such as when all pixels have been analyzed or the piece has been determined to have passed or failed inspection, the method proceeds to 718.

At 718, a map of the component can be generated, such as for situations in which an operator is required to analyze the image and determine whether the component is acceptable or unacceptable because a borderline set of image data has been generated.

In operation, method 700 allows components to be analyzed to determine whether the three-dimensional coordinates of the component are acceptable. Method 700 allows inspection to be stopped after sufficient data has been generated to determine whether the component is acceptable or not, and allows borderline values to be identified so as to allow an operator to review the inspection data to make a determination when the data is not clearly acceptable or unacceptable.

Figure 8:
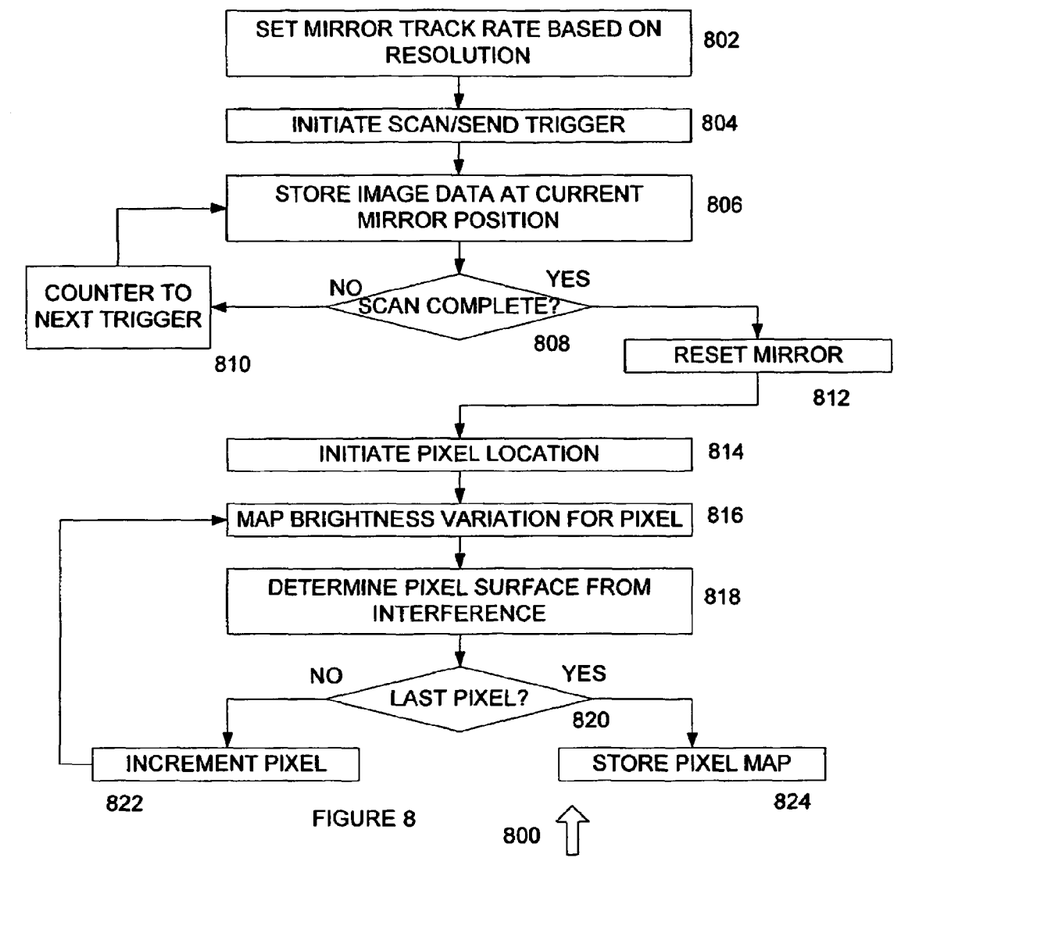
FIG. 8 is a flow chart of a method for determining surface coordinates of a component in accordance with an exemplary embodiment of the present invention.

FIG. 8 is a flow chart of a method 800 for determining surface coordinates of a component in accordance with an exemplary embodiment of the present invention. Method 800 begins at 802 where a mirror track rate is set based on a desired resolution. In one exemplary embodiment, the number of frames of data to be generated per scan can be selected based upon a track rate and desired resolution, such as where the accuracy of the surface location is a function of user specified criterion. In another exemplary embodiment, the number of optical or magnetic measurement points around the circumference of a motor can be used as an encoder to correlate motor steps or angular location to coordinates along the height axis of an inspection piece, such that a trigger is generated when a predetermined degree of rotation has been measured. The method then proceeds to 804.

At 804, the scan is initiated. In one exemplary embodiment, the scan can be initiated by moving an adjustable mirror along an axis in a plus or minus direction at a predetermined rate, using a predetermined number of encoder steps, or in other suitable manners. Likewise, scanning can be initiated by moving a component support or other suitable systems or devices. The method then proceeds to 806.

At 806, a frame of image data is stored at the current mirror position, such as after receipt of a trigger generated by counting encoder steps. In one exemplary embodiment, the generation of a frame of image data can occur at a rate much faster than the movement of the mirror, such that compensation for the pixels of image data are generated is not required. Likewise, where the relative motion of the mirror or other component creating the z-axis position differential occurs at a rate where compensation is required, such as where the z-axis coordinate of pixels that are first scanned as different from the z-axis coordinate pixels that are scanned last, or where the brightness data for each pixel may vary by a significant amount, the image data can include an indication of this differential z-axis location, an interpolation of the brightness data, or other suitable correction data. In another exemplary embodiment, an on-the-fly process can be used to determine the surface coordinates corresponding to each pixel, such as by using a moving average of pixel brightness where the surface coordinates are determined when the average brightness decreases by a predetermined amount. In this exemplary embodiment, storage of each frame of pixel data and the subsequent analysis of steps 814 through 824 can be avoided. Likewise, other suitable processes can be used. The method then proceeds to 808.

At 808, it is determined whether the scan has been completed. If the scan has not been completed, the method proceeds to 810 where it is determined whether the next trigger or other suitable indications have been received. If it is determined at 808 that a scan is complete, the method proceeds to 812 where the mirror is reset. In one exemplary embodiment, the mirror can be used to track in one direction only, such that after a component is scanned, the mirror is returned to a starting position to provide reliable tolerance estimates of a location point for the initiation of the scan. Likewise, the mirror can be moved in a first direction for scanning a first component, such as to generate frames of image data along the z-axis starting at (z=0) and ending at (z=maximum height of component features). Likewise, the next scan can be performed in the opposite direction, such as starting at (z=maximum height of component features) and ending at (z=0). Other suitable procedures can be used. Likewise, z-axis control components other than the mirror can be reset, such as a component support. The method then proceeds to 814.

At 814, the pixel location is initiated. In one exemplary embodiment, pixel location initiation can include starting at pixel (0,0) and ending at pixel (N,M). In this exemplary embodiment, each pixel is analyzed individually, serially, or parallel processors can be used for analyzing sets of pixels in parallel. Likewise, pixel location can be initiated based on the z-axis coordinate where all pixels are analyzed in parallel. In yet another exemplary embodiment, pixel analysis can occur during frame scanning, such that pixels are analyzed after it is determined that the variations in pixel brightness have been measured to a sufficient degree to determine the surface corresponding the pixel location. The method then proceeds to 816.

At 816, the brightness variation is mapped for each pixel. In one exemplary embodiment, a set of pixel data for pixels at an (x,y) coordinate can be retrieved for each z coordinate value, and changes in brightness value can be mapped, such as by determining a center line, determining the deviation from the center line data, or other suitable procedures. The method then proceeds to 818.

At 818, pixel surface data is determined from interference principles. In one exemplary embodiment, the surface of the component corresponding to the pixel location can be determined based on finding the center fringe of an interference pattern, based on finding the mid-point of an interference region, based on an envelope of the interference region, using magnitude and direction orientation settings, or by other suitable procedures. The method then proceeds to 820.

At 820, it is determined whether the last pixel has been analyzed. In one exemplary embodiment, if the pixels are being used to analyze damage, then the determination at 820 can be whether the damage exceeds predetermined allowable bounds. Likewise, where pixels are being examined individually on a serial basis, it can be determined whether the pixel at the (N,M) location has been analyzed. If it is determined at 820 that the last pixel has been analyzed, the method proceeds to 824 and the pixel map is stored, such as a map of surface location values for each pixel that can be used to analyze the image data. Otherwise, the method proceeds to 822 where the pixel is incremented, such as by going to the next pixel in the series where serial pixel analysis is being performed or in other suitable manners.

In operation, method 800 allows the three-dimensional coordinates for the surface of a component to be determined using interferometry. Method 800 uses an N×M array of pixel data or other suitable sets of data, and determines the surface location at each point based upon brightness variations that occur as an interference pattern is moved axially in the z-axis direction along a component. This process results in a maximum brightness variation occurring when the surface corresponds to the location of an interference pattern center. In this manner, the surface of the component corresponding to the location of each pixel can be determined, and a three-dimensional map of the component can be generated.

Figure 9:
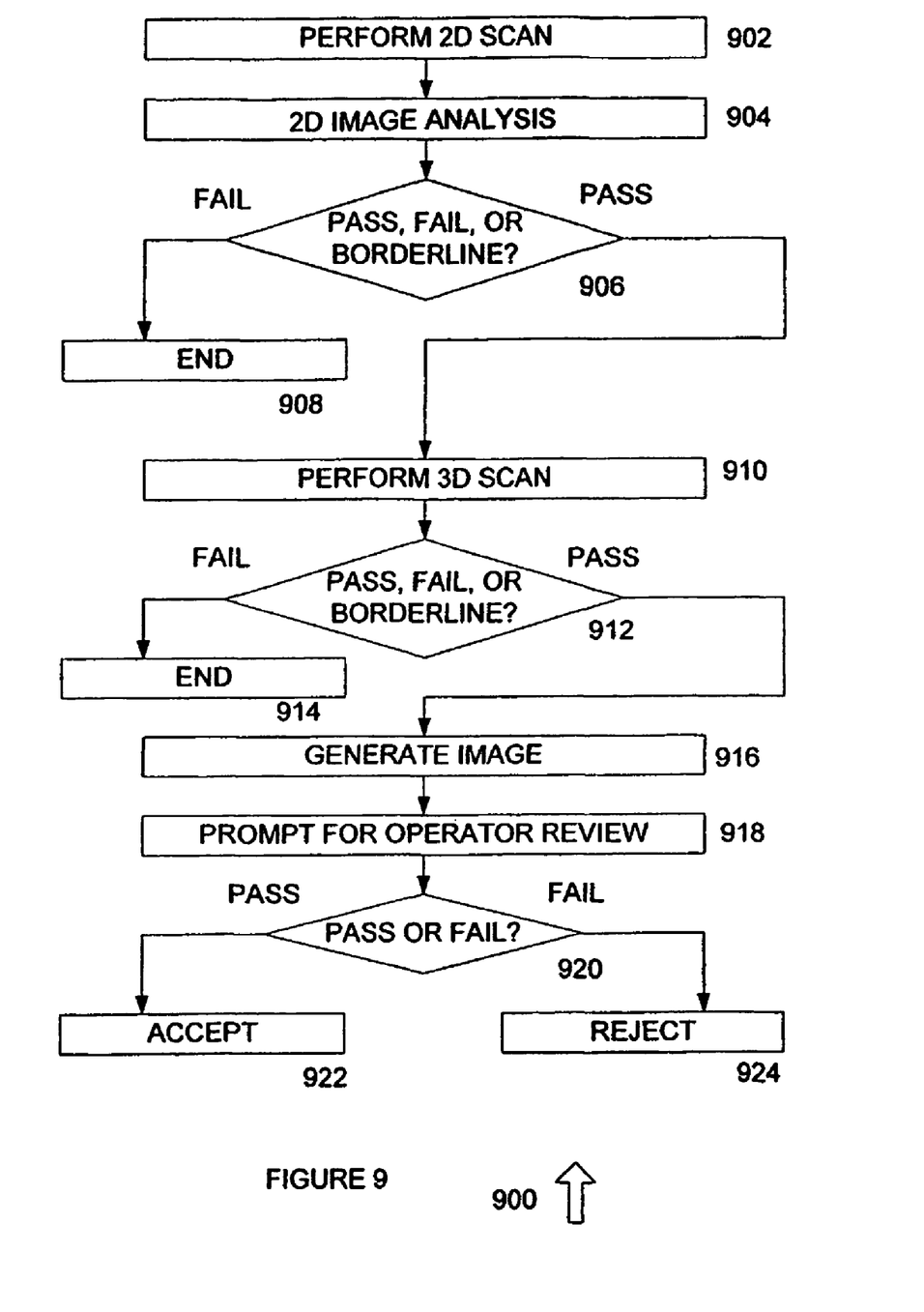
FIG. 9 is a flowchart of a method for performing component inspection in accordance with an exemplary embodiment of the present invention.

FIG. 9 is a flowchart of a method 900 for performing component inspection in accordance with an exemplary embodiment of the present invention. Method 900 uses a two-dimensional analysis for performing component testing, and uses three-dimensional analysis when two-dimensional analysis results in indeterminate results or otherwise indicates the need for further analysis. Likewise, method 900 can be used to perform a two-dimensional analysis for certain image features and a three-dimensional analysis for other image features, such as where the entire component is analyzed using 2D analysis but only a section of the component is analyzed using 3D analysis.

Method 900 begins at 902 where a 2D scan is performed. In one exemplary embodiment, the 2D scan can be performed by illuminating a component with monochromatic or polychromatic light that does not include any interference fringing phenomena. The light can be coherent or noncoherent. The method then proceeds to 904.

At 904, the 2D image data is analyzed, such as by using traditional image analysis techniques. These image analysis techniques can detect faults based on brightness value variations in the 2 dimensional image data. Likewise, a histogram of brightness values can be created, and pass/fail criteria based on the number of excursions, slopes, or other suitable histogram data can be used to analyze the data. The method then proceeds to 906.

At 906, it is determined whether the data indicates that the component passes inspection, fails inspection, or is borderline. If it is determined at 906 that the component has passed inspection, the method proceeds to 908 and ends. Otherwise, the method proceeds to 910. In another alternative embodiment, if the component fails, then the component is rejected, and the method only proceeds to 910 if the component results are borderline. In yet another exemplary embodiment, if the component fails, then the component is rejected, but if the component passes or is borderline, then the method proceeds to 910 for performance of a three-dimensional analysis.

At 910, a three-dimensional scan is performed on the component. In one exemplary embodiment, the three-dimensional scan can be performed using interferometry techniques, such as where a number of N×M frames of pixel data of the component are generated while the component is illuminated with light that is generating an interference pattern. The successive frames of image data can be used to generate a three-dimensional map of the component or other suitable three-dimensional mapping techniques can be used. The method then proceeds to 912.

At 912, it is determined whether the component has passed, failed, or is borderline. In one exemplary embodiment, the component can be analyzed to determine the size of defects or flaws, such as the surface area of a defect or flaw, the volume of a defect or flaw (such as an amount of material missing from or added to areas), the average or maximum height or depth of the defect or flaw, whether a feature is missing, or other suitable analysis of three-dimensional data can be performed. If it is determined at 912 that the component has passed, the method proceeds to 914 and terminates. In another alternative embodiment, if the component fails, then the component is rejected, and the method only proceeds to 916 if the component results are borderline. In yet another exemplary embodiment, if the component fails, then the component is rejected, but if the component passes or is borderline, then the method proceeds to 916 for operator review. Otherwise, the method proceeds to 916 where image data of the component is generated. In one exemplary embodiment, a three-dimensional image can be generated for review by an operator, such as where the component data is borderline or indeterminate. The method then proceeds to 918 where an operator is prompted to review the image data and make a determination of whether to accept or reject the data. The method then proceeds to 920.

At 920, it is determined whether the operator has indicated if the component passes or fails inspection. In one exemplary embodiment, the operator can use one or more analysis tools, such as shape tools, volume tools, templates showing acceptable and unacceptable damage criteria or other suitable data. If it is determined at 920 that the component passes, the method proceeds to 922 where the component is accepted. Otherwise, the method proceeds to 924 and the component is rejected.

In operation, method 900 allows a component to be inspected using a sequential process of two-dimensional and three-dimensional image data analysis, such as to decrease the amount of time that is required for component inspection. Method 900 performs an initial two-dimensional analysis to locate components that are readily determined to be acceptable or objectionable. If additional analysis is required to clear the component, then a 3D analysis can be performed, such as when the component is borderline. Likewise, if additional 3D analysis is only to be performed on components that pass 2D analysis, method 900 allows such performance to be performed only on the components that are first determined to be acceptable, and eliminates unnecessary processing of components that are determined to be unacceptable.

Although exemplary embodiments of a system and method of the present invention been described in detail herein, those skilled in the art will also recognize that various substitutions and modifications can be made to the systems and methods without departing from the scope and spirit of the appended claims.

What is claimed is:

1. A system for inspecting a component comprising:
an image data system generating image data;
an interferometry inspection system coupled to the image data system, the interferometry inspection system receiving the image data and generating inspection pass/fail data based on surface coordinate data generated using interferometry; and
a tracking acceleration system generating tracking acceleration data.

2. The system of claim 1 wherein the interferometry inspection system further comprises a pixel mapping system receiving the surface coordinate data and generating pixel map data of a surface.

3. The system of claim 1 wherein the interferometry inspection system comprises a brightness variation system receiving the image data and storing a plurality of frames of image data.

4. The system of claim 3 wherein the interferometry inspection system further comprises a data compression system receiving the surface coordinate data and eliminating one or more pixel data values.

5. The system of claim 1 wherein the interferometry inspection system comprises a mirror position system receiving mirror position data and correlating the mirror position data with the image data.

6. The system of claim 1 wherein the interferometry inspection system further comprises a track rate controller generating mirror position control data.

7. The system of claim 1 wherein the interferometry inspection system comprises a pixel surface location system receiving the image data and generating pixel surface data.

8. The system of claim 1 wherein the interferometry inspection system comprises a brightness plotting system receiving the image data and generating pixel brightness plot data.

9. The system of claim 1 wherein the interferometry inspection system comprises a brightness plotting system receiving the image data and generating pixel midpoint data.

10. The system of claim 1 wherein the interferometry inspection system comprises a fringe counting system receiving the image data and generating fringe counting data.

11. The system of claim 1 wherein the interferometry inspection system comprises a missing feature system receiving the surface coordinate data and generating missing feature data.

12. The system of claim 1 wherein the interferometry inspection system comprises a defect volume system receiving the surface coordinate data and generating defect volume data.

13. The system of claim 1 wherein the interferometry inspection system comprises a defect area system receiving the surface coordinate data and generating defect area data.

14. The system of claim 1 wherein the interferometry inspection system comprises a defect depth/height system receiving the surface coordinate data and generating defect depth or height data.

15. A method for inspecting a component comprising:
generating two or more sets of image data of the component;
determining brightness data for each of a plurality of pixels in each set of image data;
using a change in brightness data for each pixel to determine surface data for a height of each pixel based on interferometry;
using the surface data to generate a three-dimensional surface map;
generating inspection pass/fail data using the three-dimensional surface map and and accepting a component where generated inspection pass/fail data indicates the component is acceptable.

16. The method of claim 15 wherein using the change in brightness data for each pixel to determine the surface data for each pixel based on interferometry comprises determining the center interference fringe for each pixel.

17. The method of claim 15 wherein using the change in brightness data for each pixel to determine the surface data for each pixel based on interferometry comprises determining the surface data for each pixel based on the minima and maxima of the brightness data for each pixel.

18. The method of claim 15 wherein determining the brightness data for each of the plurality of pixels in each set of image data further comprises:

determining whether the change in brightness data for each pixel exceeds a predetermined value; and compressing the brightness data for each pixel if the change does not exceed the predetermined value.

19. A method for inspecting a component comprising:

generating two or more sets of image data of the component;

determining brightness data for each of a plurality of pixels in each set of image data;

using a charge in brightness data for each pixel to determine surface data for each pixel based on interferometry, wherein using the change in brightness data for each pixel to determine the surface data for each pixel based on interferometry comprises:

counting the number of interference fringes for each pixel; and setting the surface data for each pixel based on the number of interference fringes;

using the surface data to generate inspection pass/fail data and accepting a component where generated inspection pass/fail data indicates the component is acceptable.

20. A method for inspecting a component comprising:

generating two or more sets of image data of the component;

determining brightness data for each of a plurality of pixels in each set of image data;

using a change in brightness data for each pixel to determine surface data for each pixel based on interferometry;

wherein using the change in brightness data for each pixel to determine the surface data for each pixel based on interferometry comprises:

calculating a moving average for a predetermined number of pixels; and determining the surface data based on when the moving average decreases by an amount greater than a predetermined amount;

using the surface date to generate a three-dimensional surface map of the component;

generating inspection pass/fail data using the three-dimensional surface map and accepting a component where generated inspection pass/fail data indicates the component is acceptable.

21. A method for inspecting a component comprising:

moving the mirror of an interference system relative to the component at a predetermined rate to generate changing interference patterns on features of the component, wherein the predetermined rate includes a first rate and a second rate;

using a change in brightness value for each of a plurality of pixels to determine surface data for each pixel based on interference principles;

using the surface data to generate inspection pass/fail data and accepting a component where generated inspection pass/fail data indicates the component is acceptable.

22. The method of claim 21 wherein the predetermined rate includes a first rate that is used when an image data is being generated and a second rate that is used when image data is not being generated.

23. A method for inspecting a component comprising:

moving the mirror of an interference system relative to the component at a predetermined rate to generate changing interference patterns on features of the component, wherein the predetermined rate is selected based on a predetermined resolution;

using a change in brightness value for each of a plurality of pixels to determine surface data for each pixel based on interference principles;

using the surface data to generate inspection pass/fail data and accepting a component where generated inspection pass/fail data indicates the component is acceptable.

24. A method for inspecting a component using interferometry comprising:

generating surface coordinate data of pixel heights for the component using interferometry;

generating component inspection pass/fail data based on the surface coordinate data and accepting a component where generated inspection pass/fail data indicates the component is acceptable.

25. The method of claim 24 wherein generaUng component inspection pass/fail data based on the surface coordinate data comprises:

determining a number of pixels having surface coordinate data outside of a predetermined range; and generating missing feature data if the number of pixels is greater than a predetermined number.

26. A method for inspecting a component using interferometry comprising:

generating surface coordinate data using interferometry; and generating component inspection pass/fail data based on the surface coordinate data, wherein generating component inspection pass/fail data based on the surface coordinate data comprises:

summing a volume of each pixel having surface coordinate data different from expected surface data to produce a total volume;

generating inspection fail data if the total volume is greater than a predetermined volume and accepting a component where generated inspection pass/fail data indicates the component is acceptable.

27. A method for inspecting a component using interferometry comprising;

generating surface coordinate data using interferometry; and generating component inspection pass/fail data based on the surface coordinate data, wherein generating component inspection pass/fail data based on the surface coordinate data comprises:

summing an area of each pixel having surface coordinate data different from expected surface data to produce a total area;

generating inspection fail data if the total area is greater than a predetermined area and accepting a component where generated inspection pass/fail data indicates the component is acceptable.

28. A method for inspecting a component using interferometry comprising:

generating surface coordinate data using interferometry; and generating component inspection pass/fail data based on the surface coordinate data, wherein generating component inspection pass/fail data based on the surface coordinate data comprises:

determining a maximum depth or height of each pixel having surface coordinate data different from expected surface data;

generating inspection fail data if the maximum depth or height is greater than a predetermined depth or height and accepting a component where generated inspection pass/fail data indicates the component is acceptable.

29. A method for inspecting a component using interferometry comprising:
  generating surface coordinate data using interferometry; and
  generating component inspection pass/fail data based on the surface coordinate data, wherein generating component inspection pass/fail data based on the surface coordinate data comprises:
    determining an average depth or height of each pixel having surface coordinate data different from expected surface data;
    generating inspection fail data if the average depth or height is greater than a predetermined average depth or height and accepting a component where generated inspection pass/fail data indicates the component is acceptable.

30. A system for inspecting a component comprising:
  a 2D inspection system receiving image data and generating 2D inspection pass/fail data without using interference fringing; and
  an interferometry inspection system receiving image data and generating interferometry inspection pass/fail data;
  wherein the interferometry inspection system receives the image data after the 2D inspection system generates 2D inspection pass/fail data.

31. The system of claim 30 wherein the interferometry inspection system only receives the image data after the 2D inspection system generates 2D inspection pass data.

32. The system of claim 30 wherein the interferometry inspection system only receives the image data after the 2D inspection system generates 2D inspection fail data.

33. The system of claim 30 wherein the interferometry inspection system only receives the image data after the 2D inspection system generates 2D inspection borderline data.

34. A method for inspecting a component using interferometry comprising:
  performing a 2D inspection of the component without using interference fringing and generating 2D inspection pass/fail data; and
  performing an interferometry inspection of the component based on the 2D inspection pass/fail data and generating interferometry inspection pass/fail data; and
  accepting a component where generated interferometry inspection pass/fail data indicates the component is acceptable.

35. The method of claim 34 wherein performing the interferometry inspection of the component based on the 2D inspection pass/fail data comprises only performing the interferometry inspection of the component if the 2D inspection pass/fail data indicates a failure.

36. The method of claim 34 wherein performing the interferometry inspection of the component based on the 2D inspection pass/fail data comprises only performing the interferometry inspection of the component if the 2D inspection pass/fail data indicates a pass.

37. The method of claim 34 wherein performing the interferometry inspection of the component based on the 2D inspection pass/fail data comprises only performing the interferometry inspection of the component if the 2D inspection pass/fail indicates a borderline result.

38. A system for inspecting a component comprising:
  a 2D inspection system receiving image data and generating 2D inspection pass/fail data;
  an interferometry inspection system receiving image data and generating interferometry inspection pass/fail data; and
  an interference system having a retractable shutter, where the 2D inspection system receives image data when the shutter is blocking, and the interferometry system receives image data when the shutter is non-blocking;
  wherein the shutter remains blocking when the 2D inspection system generates 2D inspection pass data.

39. The system of claim 38 wherein the component is one of the group comprising a silicon wafer, a dle, a silicon wafer on a film frame, a die on a film frame, a die in a gel pack, a die on a die support, a die on a belt, a die in a tray, a die in a waffle pack, a semiconductor component, a chip-scale package, a bumped wafer, and a die having a ball grid array.

40. A system for inspecting a component comprising:
  a 2D inspection system receiving image data and generating 2D inspection pass/fail data;
  an interferometry inspection system receiving image data and generating interferometry inspection pass/fail data; and
  an interference system having a retractable shutter, where the 2D inspection system receives image data when the shutter is blocking, and the interferometry system receives image data when the shutter is non-blocking;
  wherein the shutter remains blocking when the 2D inspection system generates 2D inspection fail data.

41. A system for inspecting a component comprising:
  a 2D inspection system receiving image data and generating 2D inspection pass/fail data;
  an interferometry inspection system receiving image data and generating interferometry inspection pass/fail data; and
  an interference system having a retractable shutter, where the 2D inspection system receives image data when the shutter is blocking, and the interferometry system receives image data when the shutter is non-blocking;
  wherein the shutter remains blocking when the 2D inspection system generates 2D inspection borderline data.

42. A method for inspecting a component comprising:
  blocking a mirror of an interference system to illuminate the component with a first beam of light to perform 2D inspection;
  receiving image data of the component and generating 2D inspection pass/fail data;
  unblocking the mirror of the interference system to illuminate the component with the first beam of light and a second beam of light to perform interferometry inspection;
  receiving image data of the component and generating interferometry inspection pass/fail data and accepting a component where at least one of generated 2D inspection pass/fail data and generated interferometry inspection pass/fail indicates the component is acceptable.

43. The method of claim 42 wherein blocking the mirror of the interference system stops a second beam of light from a beam splitter from illuminating the component.

44. The method of claim 42 wherein unblocking the mirror of the interference system to illuminate the component with the first beam of light and the second beam of light is performed when the 2D inspection system generates 2D inspection pass data.

45. The method of claim 42 wherein unblocking the mirror of the interference system to illuminate the component with the first beam of light and the second beam of light is performed when the 2D inspection system generates 2D inspection fail data.

46. The method of claim 42 wherein unblocking the mirror of the interference system to illuminate the component with the first beam of light and the second beam of light is performed when the 2D inspection system generates 2D inspection borderline data.

47. The method of claim 42 wherein the component is one of the group comprising a silicon wafer, a die, a silicon wafer on a film frame, a die on a film frame, a die in a gel pack, a die on a die support, a die on a belt a die in a tray, a die in a waffle pack, a semiconductor component, a chip-scale package, a bumped wafer, and a die having a ball grid array.

* * * * *